(12) United States Patent
Bayer et al.

(10) Patent No.: US 7,156,839 B2
(45) Date of Patent: Jan. 2, 2007

(54) MULTI-PURPOSE SURGICAL INSTRUMENT

(75) Inventors: Hanspeter R. Bayer, Meriden, CT (US); Russell Heinrich, Madison, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 607 days.

(21) Appl. No.: 10/428,706

(22) Filed: May 2, 2003

(65) Prior Publication Data

US 2004/0068253 A1 Apr. 8, 2004

Related U.S. Application Data

(63) Continuation of application No. 10/264,555, filed on Oct. 4, 2002, now abandoned.

(51) Int. Cl.
*A61B 17/00* (2006.01)
*A61B 17/32* (2006.01)
*B25G 1/01* (2006.01)
*B25F 1/04* (2006.01)

(52) U.S. Cl. .................. 606/1; 606/167; 606/205; 81/489; 7/167

(58) Field of Classification Search ............ 606/1, 606/205, 167, 170, 148; 206/370, 372, 375; 81/124.4, 489, 498; 473/406; 362/119; 7/167, 168, 158

See application file for complete search history.

(56) References Cited

U.S. PATENT DOCUMENTS

| 5,086,674 | A | * | 2/1992 | Her | 81/124.4 |
| 5,336,231 | A | * | 8/1994 | Adair | 606/1 |
| 5,388,824 | A | * | 2/1995 | Reimers | 473/406 |
| 5,431,672 | A | | 7/1995 | Doucette et al. | |
| 5,517,885 | A | * | 5/1996 | Feng | 81/490 |
| 5,925,064 | A | | 7/1999 | Meyers et al. | |
| 5,984,932 | A | * | 11/1999 | Yoon | 606/148 |
| 6,027,224 | A | * | 2/2000 | Schnell | 362/119 |
| 6,159,200 | A | | 12/2000 | Verdura et al. | |
| 6,165,184 | A | | 12/2000 | Verdura et al. | |
| 2002/0098138 | A1 | | 7/2002 | Gabele | |

\* cited by examiner

*Primary Examiner*—Julian W. Woo

(57) ABSTRACT

A multi-instrument surgical tool for use during hand-assisted laparoscopic surgery includes a housing having a plurality of ports disposed therein which are each dimensioned to slidingly house one of a plurality of surgical instruments for selective deployment from the case. The housing also includes a corresponding plurality of elongated channels each in communication with a respective one of the plurality of ports. Each of the instruments including an actuator which is movable within a respective channel from a first position wherein the instrument is at least partially housed within the housing to a second position wherein the actuator is disengaged from the respective channel and the actuator is freely operable to actuate the instrument for its intended purpose.

15 Claims, 8 Drawing Sheets

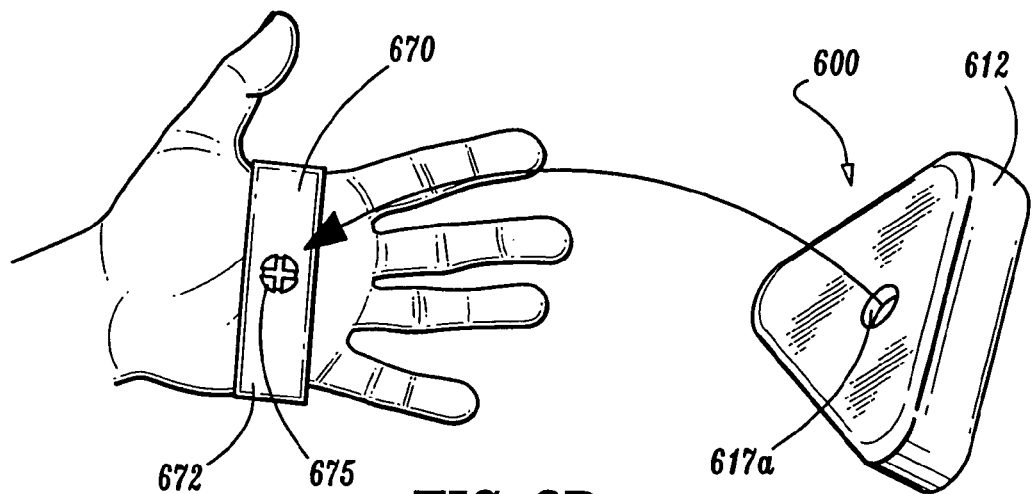
FIG. 3B
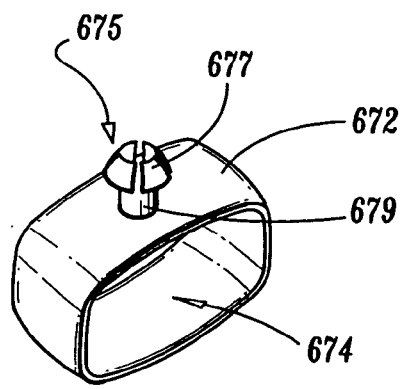
FIG. 3A
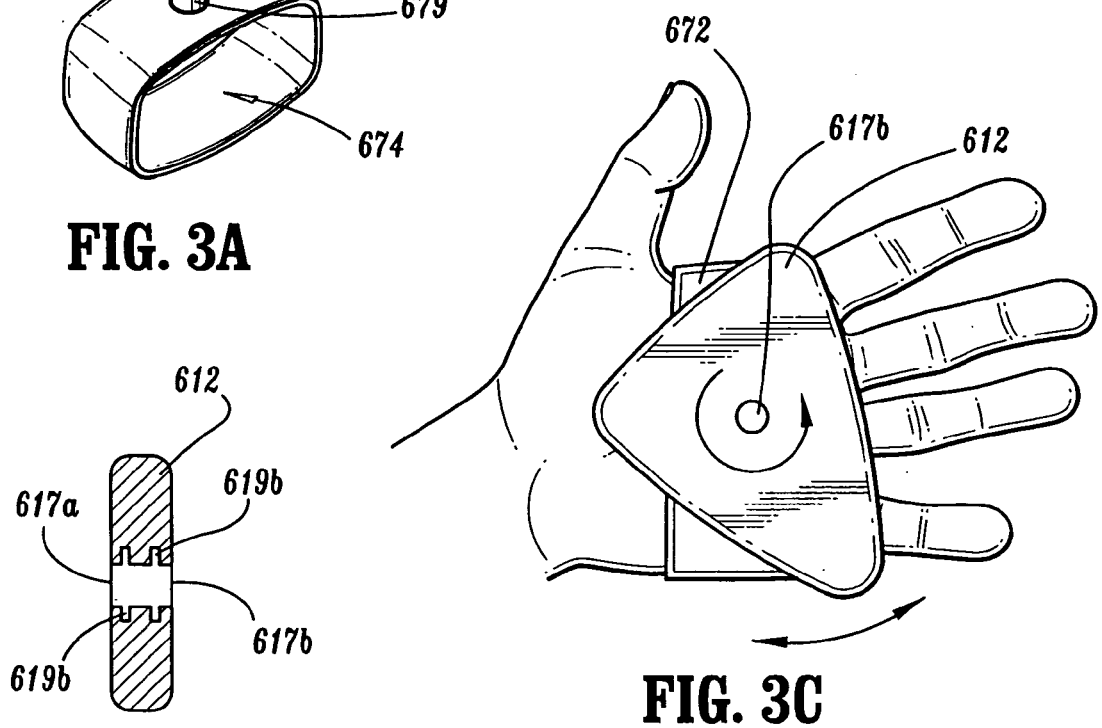
FIG. 3D
FIG. 3C

MULTI-PURPOSE SURGICAL INSTRUMENT

CROSS REFERENCE TO RELATED APPLICATIONS

This application is a Continuation of U.S. patent application Ser. No. 10/264,555, filed on Oct. 4, 2002, which is now abandoned, the disclosure of which is hereby incorporated by reference herein.

BACKGROUND

1. Technical Field

The present invention relates to the field of surgical tools and more particularly to a multipurpose surgical tool for use during hand-assisted laparoscopic surgery, minimally invasive surgical procedures and traditional open surgical procedures.

2. Background of Related Art

Open surgery, in general, has remained the procedure of choice for many surgeons since it enhances a surgeon's view of the operating cavity and allows a surgeon to readily palpate the internal organs as needed during a surgical procedure. However, the relatively large incisions required can often be traumatic for patients and may result in a prolonged healing process. As a result and as an alternative to traditional open surgery, many surgeons utilize minimally invasive surgical techniques to treat tissue remotely through small incisions utilizing specialized endoscopic instruments. More particularly, endoscopic instruments are inserted into the patient through a cannula or port that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the smaller cannulas.

Certain endoscopic surgical procedures require cutting, cauterizing and/or sealing blood vessels and/or vascular tissue which, typically, requires the surgeon to insert different instruments through the working lumen of the endoscope to treat the tissue. As can be appreciated, this simply adds to the overall complexity of the operation since it requires the repeated exchange of surgical instruments through the working lumen to perform the different tasks associated with the particular surgery involved.

There are also some disadvantages to endoscopic surgery. For example, endoscopic instruments tend to limit a surgeon's ability to freely manipulate organs and often limit the surgeon's view of the operating cavity. Moreover, when using endoscopic instruments, the surgeon loses tactile feedback of the tissue which can play an important role in some surgical procedures. Further, when the particular surgery dictates the removal of a tissue specimen, the tissue must be either be morselized to fit through the trocar lumen or the surgeon must create a larger opening to remove the specimen intact essentially abandoning the benefits associated with endoscopic surgery.

Combining the advantages of the traditional and the laparoscopic techniques for abdominal surgery is commonly referred to as "hand-assisted laparoscopic surgery" (HALS). In this procedure, the normal laparoscopic small puncture openings are made with the exception that one opening is made late in the procedure and large enough to allow a surgeon's hand to pass through the opening to manipulate tissue, deliver new instruments into the operating cavity and/or remove tissue specimens. HALS attempts to restore dexterity and tactile feedback by allowing the surgeon to place one hand within the operating space through a hand port. Once the hand is in the operating space, it can be used to manipulate and palpate tissues in much the same way as it is used in open surgical procedures.

When performing surgery in the abdominal cavity, air or gas is typically introduced to create a condition known as "pneumoperitoneum". Ideally, HALS procedures are performed while maintaining the pneumoperitoneum which eliminates re-insufflation of the surgical cavity. As can be appreciated, if a surgeon's hand has to be removed to retrieve additional surgical instruments, the cavity will deflate and subsequent re-insufflation of the pneumoperitoneum may be required. This simply prolongs the overall surgical procedure and makes HALS surgery very tedious especially when multiple instruments must be utilized during the surgical procedure. As a result, a need exists to develop an improved surgical tool which reduces the need to remove the instruments useful for performing hand assisted laparoscopic surgical procedures.

SUMMARY

The present disclosure relates to a multipurpose surgical tool for use in minimally invasive surgical procedures such as Hand Assisted Laparoscopic Surgery (HALS). Additionally, the multipurpose surgical tool of the present disclosure may be used in traditional open surgical procedures.

During HALS surgery, the multipurpose surgical tool may be inserted, in the hand, through a hand port which is made during the course of the surgery. The surgeon manipulates the tool as needed and switches among the plurality of specialized surgical instruments encased within the tool. As can be appreciated, this eliminates the need for the surgeon to remove his/her hand from the operating cavity to switch among instruments.

The present disclosure includes a multi-instrument surgical tool for use during hand-assisted laparoscopic surgery which includes a housing or casing having a plurality of ports disposed therein. The housing includes a corresponding plurality of elongated channels each in communication with a respective one of the plurality of ports. Each of the ports is dimensioned to slidingly house one of a plurality of surgical instruments therein for selective deployment from the housing. The instruments each include an actuator which is movable within a respective channel from a first position wherein the instrument is at least partially housed within the housing to a second position wherein the actuator is disengaged from the respective channel and the actuator is freely operable to actuate the instrument.

In one embodiment, the housing includes two ports for slidingly housing two instruments. Preferably, the ports are disposed adjacent one another, however, in an alternate embodiment, the ports are disposed on opposite sides of the housing. In yet another embodiment, the housing is generally triangular and includes three instruments disposed therein.

Preferably, the instruments are selected from a group consisting of: needle holders; needle drivers; graspers; forceps; vessel sealing devices; dissectors; resectors; probes; morselators; ultrasonic instruments; video-assisted devices; clip appliers; surgical staplers; coagulators; bipolar an mechanical scissors; irrigation instruments; and suction instruments.

In one embodiment, the housing includes a mechanical interface or aperture disposed on the outer periphery thereof which selectively engages a corresponding mechanical interface or press-lock which is affixable to a surgeon's hand by a clip or strap. Ideally, the mechanical interfaces are rotatable relative to one another which facilitates selection of one of the plurality of instruments within the housing.

Preferably, one of the plurality of instruments is a surgical scalpel which includes proximal and distal ends. The proximal end is dimensioned to slideably engage one of the ports of the housing and the distal end includes a cutting edge. A safety guard is also included which is movable relative to the scalpel from a first position wherein the guard substantially covers the cutting edge of the scalpel to a second position wherein the cutting edge is exposed.

In one embodiment according to the present disclosure, the guard includes a locking tab for releasably locking the guard in the second position. Preferably, the guard is spring-biased to return to the first safety position.

In yet another embodiment according to the present disclosure, the multi-instrument surgical tool includes a housing having a plurality of recesses disposed along the outer periphery thereof. Each of the recesses is dimensioned to receive one of a plurality of surgical instruments therein. A pivot rotatably affixes each instrument to the housing such that each instrument is selectively rotatable relative to the outer periphery of the housing. An actuator is movably affixed to the surgical instrument for activating the surgical instrument for the surgical instrument's intended purpose.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

Illustrative embodiments of the subject surgical tool are described herein with reference to the drawings wherein:

FIG. 3A is a perspective view of a mounting strap for use with the surgical tool according to the present invention;

FIG. 3B is a schematic view showing the proper orientation of the mounting strap of FIG. 3A on the surgeon's hand and the method of engaging the mounting strap within a corresponding mounting slot in the outer housing of the surgical tool;

FIG. 3C is a schematic view showing the surgical tool rotationally mounted atop the mounting strap on the surgeon's hand;

FIG. 3D is a cross section of the mounting slot of FIG. 3B;

DETAILED DESCRIPTION

Figure 1A:
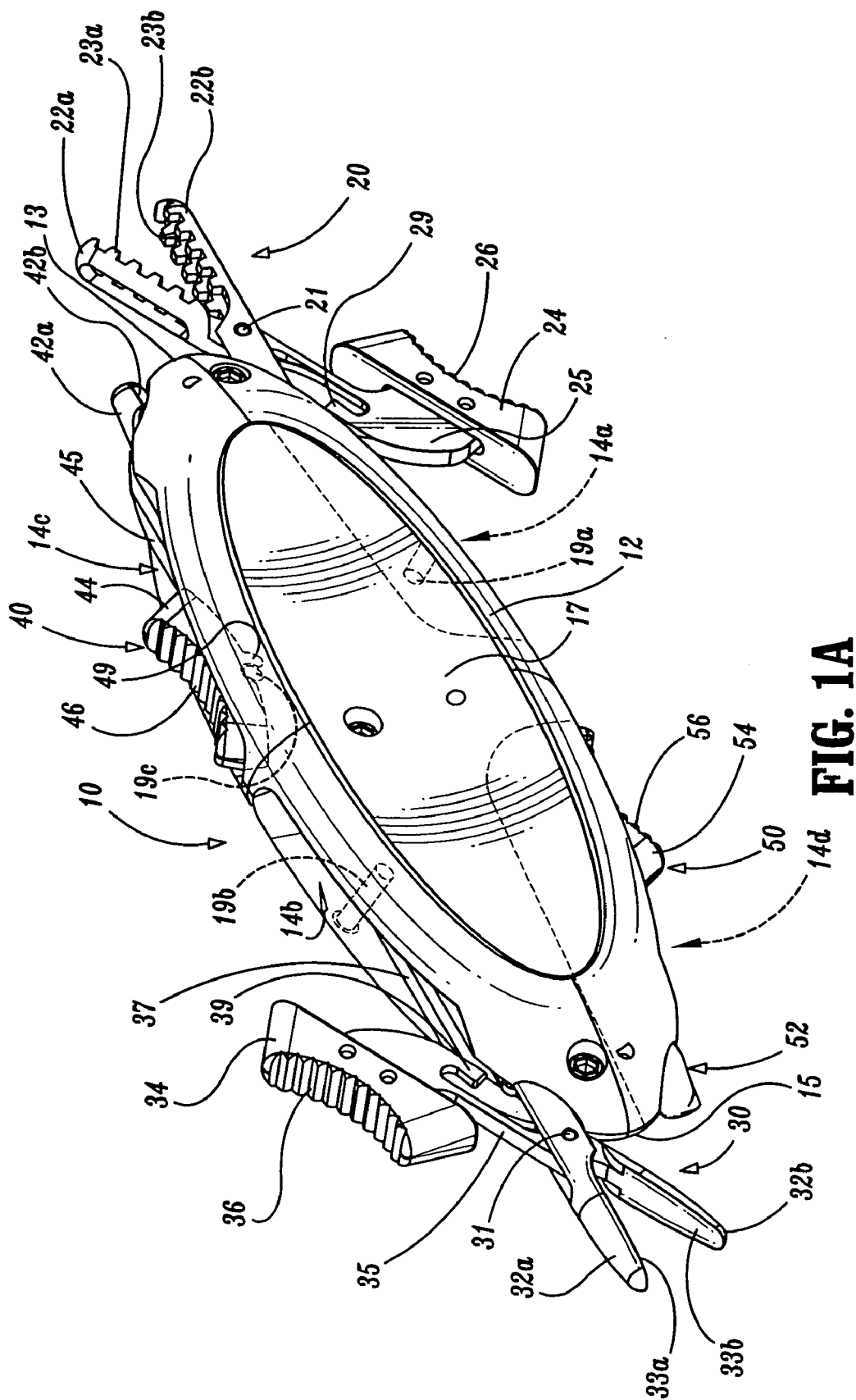
FIG. 1A is a perspective view of multi-instrument surgical tool in accordance with the present disclosure.

Preferred embodiments of the multipurpose surgical tool will be described in terms of a HALS procedure wherein the typical laparoscopic incisions are made with the exception that one, larger opening is made during the course of the procedure which is large enough to allow a surgeon's hand to pass through the opening to manipulate tissue, deliver new instruments into the operating cavity and/or remove tissue specimens. Air or gas is introduced to create the pneumoperitoneum and the HALS procedure is performed while maintaining the pneumoperitoneum.

In the drawings and in the description which follows, the term "proximal", as is traditional, will refer to the end of the instrument which is closer to the user, while the term "distal" will refer to the end which is further from the user. When described in accordance with a particular figure, the proximal and distal ends are designated for the purpose of clarification only since the nature and use of the surgical tool of the present invention enables the surgeon to freely position and rotate the tool within the surgeon's hand.

Referring now in detail to the drawing figures in which like reference numerals identify similar or identical elements, one embodiment of the present disclosure is illustrated generally in FIG. 1A and is designated therein as multipurpose surgical tool 10. Surgical tool 10 includes a case or housing 12 which has a plurality of elongated instrument slots or ports 14a, 14b, 14c and 14d defined therein for removably housing a corresponding plurality of surgical instruments 20, 30, 40 and 50, respectively. More particularly, FIG. 1A shows one embodiment of the present multipurpose surgical tool 10 which includes four surgical instruments 20, 30, 40 and 50 mounted for selective deployment within elongated ports 14a, 14b, 14c and 14d. Other embodiments are described in the figure descriptions which follow and include two-instrument (FIGS. 2A and 2B) and three-instrument (FIGS. 2C, 2D, 3B, 3C, 3E and 3F) embodiments of the multipurpose tool 10 and variations thereof.

Turning back to the embodiment shown in FIG. 1A, each of the corresponding plurality of surgical instruments, e.g., 20, is deployably housed within a corresponding elongated port 14a defined within the housing 12. With the four-instrument embodiment, two elongated ports 14a and 14c are located at one end, e.g., proximal end 13, for housing instruments 20 and 40, respectively, and two elongated ports, e.g., 14b and 14d are located at the opposite end, e.g., distal end 15, for housing instruments 30 and 50. As can be appreciated, each elongated port, e.g., 14a, is dimensioned to house the particular port's surgical instrument 20 and, as such, the relative dimensions of each port 14a may vary depending upon the particular instrument 20 being housed. Preferably, the outer surface of the housing 12 includes an ergonomically enhanced scallop to facilitate handling the tool 10 under wet operating conditions.

Alternatively, it is envisioned that all or some of the elongated ports 14a–14d may be dimensioned in a substantially uniform manner to enable an interchange of different surgical instruments 20, 30, 40 and 50. For example, it is envisioned that the surgeon may be able to select a combination of surgical instruments needed for a particular operation and assemble the tool 10 with these selected instruments prior to insertion. Preferably, the surgical instruments are selected from a group consisting of: needle holders; needle drivers; graspers; forceps; vessel sealing devices; dissectors; resectors; probes; morselators; ultrasonic instruments; video-assisted devices; clip appliers; surgical staplers; coagulators; bipolar an mechanical scissors; irrigation instruments; and suction instruments.

Moreover, it is also envisioned that certain elongated ports, e.g., 14a and 14c, may be dimensioned to accommodate one category of surgical instruments, e.g., 20 and 40, and the remaining ports 14b and 14d may be dimensioned to accommodate a second category of surgical instruments, e.g., 30 and 50. The surgeon is then able to interchange among the different categories of surgical instruments and removably engage the selected instruments in the correspondingly dimensioned or appropriate elongated ports as needed.

FIG. 1A shows the multi-purpose surgical instrument 10 having a forceps 30 deployed at the distal end 15 of the housing 12. The forceps includes two opposing jaw members 32a and 32b which are movable relative to one another about pivot 31 by virtue of an actuator 34. The jaw members 32a and 32b have inner facing surfaces 33a and 33b which cooperate to grasp tissue therebetween upon selective movement of the actuator 34. Preferably, the actuator 34 includes an ergonomically enhanced thumb tab 36 to facilitate deployment of the forceps 30 and subsequent actuation of the jaw members 32a and 32b within the operating cavity under wet conditions. A lever arm 35 is disposed between the actuator 34 and the movable jaw member, e.g., 32b, to increase the grasping pressure by mechanical advantage.

The forceps 30 also includes a locking flange 39 which engages a corresponding locking post 19b to releasably lock the forceps 30 within the corresponding elongated port 14b when retracted within housing 12. Preferably, a spring arm or leaf spring 37 biases the locking flange 39 against the locking post 19b in a pre-loaded configuration. As can be appreciated, when the actuator 34 is retracted proximally, the actuator 34 releases the locking flange 39 from the locking post 19b and allows the forceps 30 to deploy from the housing 12, i.e., the pre-loaded spring arm 37 forces the forceps 30 distally or outwardly from the housing 12 when released. Once deployed from elongated port 14b, the spring arm 37 also biases the jaws 32a and 32b in an open configuration to facilitate approximation of the tissue. Downward movement of the actuator 34 moves the jaw members 32a and 32b relative to one another about pivot 31 to grasp tissue.

A second instrument, namely, a grasping forceps 20, is shown deployed from the proximal end of the housing 12 of tool 10. Grasping forceps 20 includes two opposing jaw members 22a and 22b which are movable relative to one another about pivot 21 in much the same manner as forceps 30, i.e., by an actuator 24. Preferably, the inner facing surfaces 23a and 23b of the jaw members 22a and 22b are corrugated to facilitate grasping and manipulation of tissue.

Grasping forceps 20 includes many of the same or similar components as forceps 30. For example, grasping forceps 20 also deploys in much the same fashion as forceps 30 (i.e., depression of an ergonomically enhanced tab surface 24 to disengage the locking flange 29 from locking post 19a to release spring arm (not shown)). The forceps 20 also releasably locks into housing in a similar manner (i.e., by virtue of the mechanical engagement of the locking flange 29 and a corresponding locking post 19a). As can be appreciated, both of the forceps 20 or 30 may be deployed at any one time or the locking posts 19a and 19b may be interconnected (either mechanically or electro-mechanically) to allow deployment of only one instrument at a time.

FIG. 1A also shows third and fourth instruments 40 and 50 which are shown in a retracted or "housed" position within housing 12. These instruments 40 and 50 may include any of the instruments identified in the group described above. Preferably, each of these instruments is designed to lock within the housing 12 and deploy from the housing 12 in much the same fashion and described above with respect to forceps 20 and 30. Moreover, each of these instruments includes similar components as described above which have similar functions. For example, instrument 40 includes an actuator 44, ergonomic surface 46, lever arm 45, jaw members 42a and 42b and locking flange 49 (which engages locking post 19c). Instrument 50 includes an actuator 54, ergonomic surface 56 and jaw members 52 which again cooperate in much the same fashion as described above.

Figure 1B:
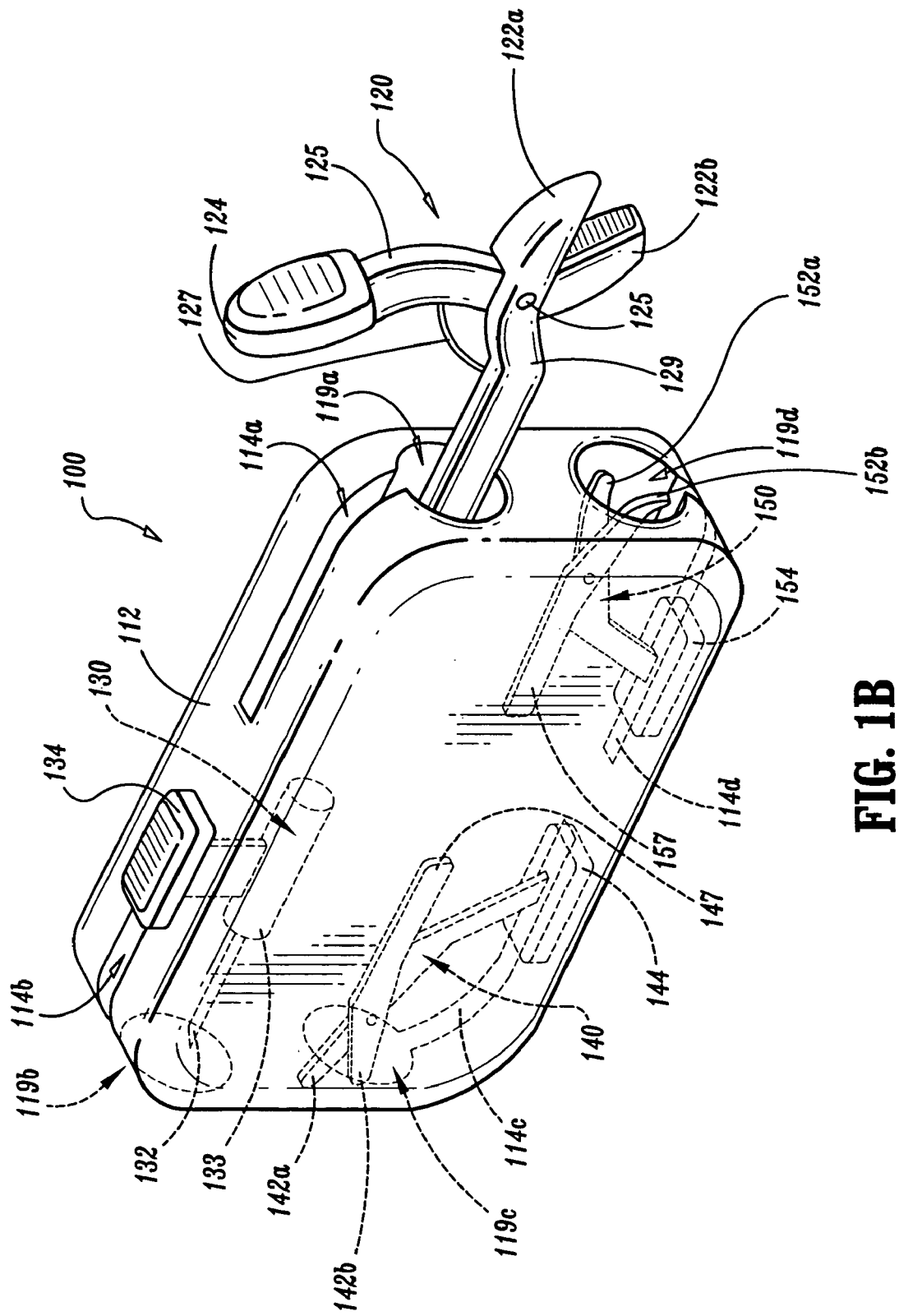
FIG. 1B is a perspective view of another embodiment of a four-instrument surgical tool in accordance with the present disclosure wherein four instruments are deployable from a rectangular-shaped housing.

FIG. 1B shows another embodiment of the surgical tool 100 of the present disclosure which shows a plurality of surgical instruments (forceps 120, needle driver 130, shears 140 and curved shears 150) for use with a rectilinear-shaped housing 112. Each instrument 120, 130, 140 and 150 is housed within a respective port 119a, 119b, 119c and 119d. Each instrument, e.g., forceps 120, is manually deployable by moving a corresponding slide-like actuator or slide member, e.g., 124, distally (or forwardly) within an elongated slot 114a disposed within the forceps' port 119a. One arm 125 of the forceps 120 is attached at one end to the slide member 124 and at the other end to a corresponding jaw member 122b. The other jaw member 122a is attached to a second arm 129 which slidingly reciprocates within port 119a. Initial distal movement of the slide member 124 rides arm 125 along slot 114a until the slide member 124 releases from slot 114a. Preferably, a spring 127 biases the slide member 124 against arm 129 which, in turn, biases the jaw members 122a and 112b in an open configuration for approximating tissue.

To retract or store the forceps 120 in the housing 112, the surgeon simply re-engages the slide member 124 within slot 114a and moves the slide member 124 proximally along slot 114a until substantially all of the forceps 120 is seated within port 119a. Preferably, the spring 127 holds the forceps 120 in friction-fit engagement within slot 114a. Alternatively, a locking mechanism (not shown) may be employed to secure the forceps 120 within port 119a.

The other instruments, namely, needle driver 130, shears 140 and curved shears 150, all include similar components and are deployable in a similar fashion. More particularly, needle driver 130 includes a slide member 134 which slides along slot 114b to selectively deploy a needle tip 132 through port 119b. Shears 140 include a slide member 144 which slides along slot 114c to selectively deploy arm 147 and blade members 142a and 142b through port 119c. Curved shears 150 include a slide member 154 which slides along slot 114d to selectively deploy arm 157 and blade members 152a and 152b through port 119d.

Figure 1C:
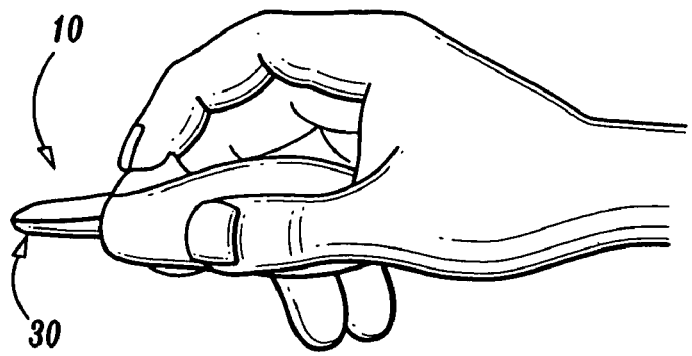
FIGS. 1C–1E are schematic representations showing various hand orientations for using the instruments of FIGS. 1A and 1B.
Figure 1D:
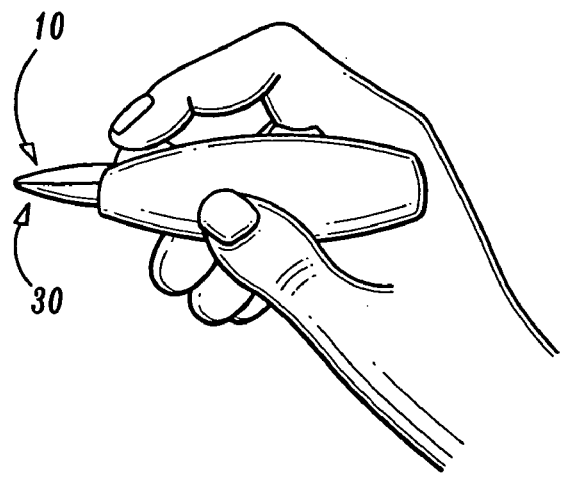
Figure 1E:
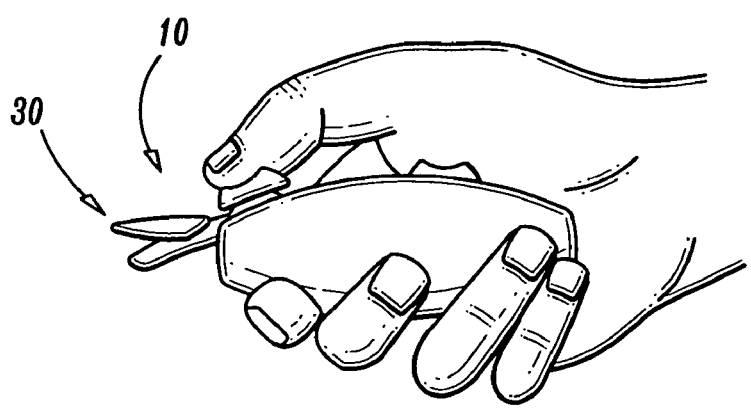

As best illustrated in FIGS. 1C–1E, the surgeon can grasp and hold the surgical tool 10, 100 in a variety of different orientations for utilizing the different instruments contained therein. Moreover, the symmetrical aspects of the surgical tool 10, 100 allow the surgeon to comfortably use the tool 10, 100 in either a right-handed or left-handed orientation.

Figure 2A:
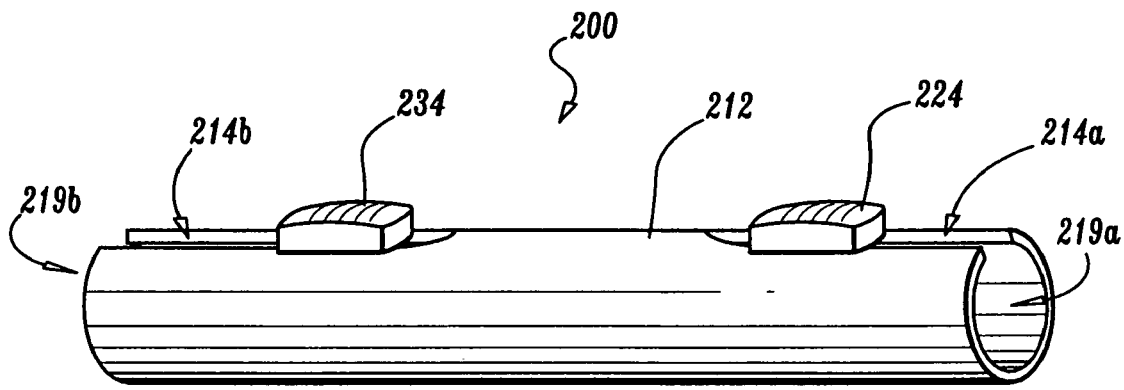
FIG. 2A is a side view showing a two-instrument surgical tool according to the present disclosure wherein the instruments are deployable from opposite sides of the housing.

FIG. 2A shows an alternative embodiment of a two-instrument surgical tool 200 which utilizes two ports 219a and 219b disposed on opposite sides of an elongated tube-like housing 212. Each of the housed instruments (not shown) includes a slide-like actuator or slide member 224 and 234 which moves along a corresponding slot 214a and 214b disposed within the housing 212 to deploy the particular instrument as needed during a given surgical procedure much in the same (or similar) manner as described above with respect to the four-instrument embodiment of FIGS. 1A–1D.

Figure 2B:
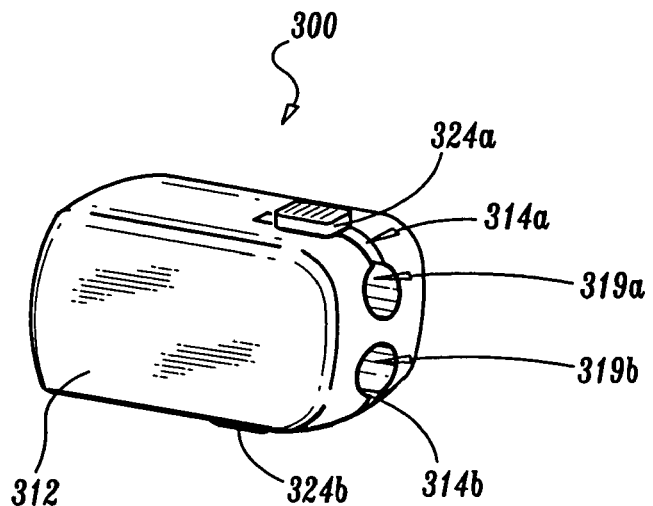
FIG. 2B is a perspective view showing a two-instrument surgical tool according to the present disclosure wherein the instruments are deployable from the same side of the housing.

FIG. 2B shows another version of a two-instrument surgical tool 300 which utilizes two ports 319a and 319b disposed adjacent one another (i.e., on the same side). Each instrument (not shown) includes an actuator 324a and 324b which moves along a corresponding slot 314a and 314b disposed within the housing 312 to deploy the particular instrument in the same (or similar) manner as described above.

Figure 2C:
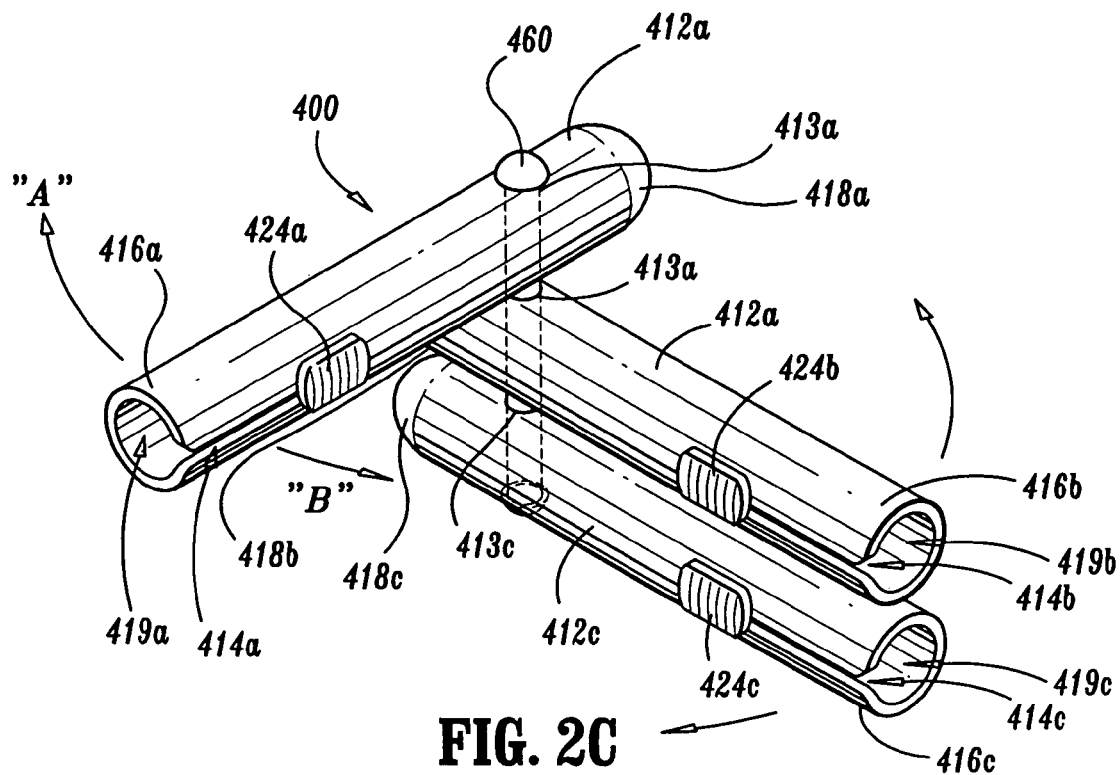
FIG. 2C is a perspective view showing a three-instrument surgical tool according to the present disclosure wherein the instruments are rotatable about a common pin for selective deployment of each instrument.

FIG. 2C shows an alternative embodiment of a three-instrument surgical tool 400 which utilizes three elongated instrument housings 412a, 412b and 412c each having a respective instrument port 419a, 419b and 419c disposed at a distal end 416a, 416b and 416c of each housing (412a, 412b and 412c). The three-instrument housings 412a, 412b and 412c are commonly attached to an elongated rod or cylinder 460 which engages each housing 412a, 412b and 412c through an aperture 413a, 413b and 413c located at a proximal end 418a, 418b and 418c of housings 412a, 412b and 412c, respectively. Each instrument (not shown) includes an actuator 424a, 424b and 424c which moves along a corresponding slot 414a, 414b and 414c disposed within housings 412a, 412b and 412c to deploy the particular instrument in the same (or similar) fashion as described with respect to FIGS. 1A–1E.

As can be appreciated, the user simply rotates one of the three housings, e.g., 412a, which contains a particular surgical instrument (not shown) about rod 460 in the direction "A" and slides the actuator 424a distally to deploy the surgical instrument for introduction into the surgical field. To select a different instrument, the user retracts slide 424a, rotates housing 412a back into vertical registration with the other housings 412b and 412c in the direction "B" and rotates a new housing, e.g., 412b, in the direction "A" to selectively deploy another instrument (not shown).

Figure 2D:
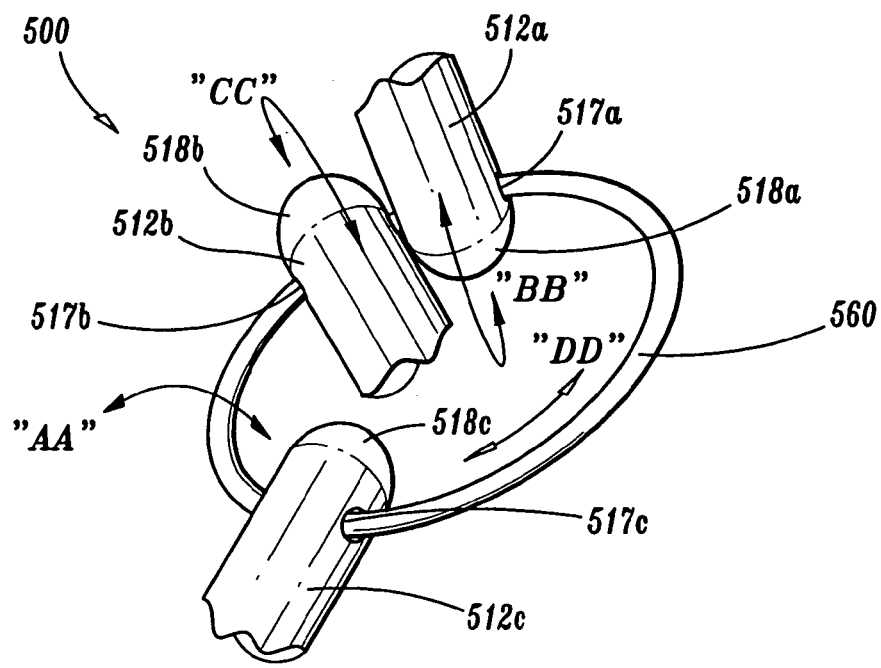
FIG. 2D is a perspective view showing a three-instrument surgical tool according to the present disclosure wherein the instruments are positionable about a key chain for selective deployment of each instrument.

FIG. 2D shows another version of the three-instrument surgical tool 500 wherein the housings 512a, 512b and 512c are commonly mounted to a key ring 560 through an aperture 517a, 517b and 517c located at the proximal end 518a, 518b and 518c of housings 512a, 512b and 512c, respectively. Much like the above three-instrument embodiment, the user simply rotates one of the three housings, e.g., 512a, about ring 560 in the direction of the arrows "AA", "BB" and "CC" to position the surgical instrument for introduction into the surgical field. The user can also move a particular instrument in the direction "DD" along ring 560 to facilitate selection and handling of the instrument in the surgical field.

FIGS. 3A–3D show another embodiment of a three-instrument surgical tool 600 which utilizes a mounting strap or hand clip 670 to permit selective rotation of the surgical tool within a surgeon's hand. Preferably, hand clip 670 includes at least one mechanical interface which mates with a corresponding mechanical interface disposed on the housing 612 of the surgical tool 600. More particularly and as shown in FIGS. 3A and 3B, hand clip 670 includes a press-lock fitting 675 which mechanically engages a corresponding aperture 617a (or 617b) located within the outer periphery of the housing 612. As best shown in FIGS. 3A and 3D, the press lock is designed for snap-fit engagement within aperture 617a (or 617b).

More particularly, the press-lock includes a segmented top portion 677 which is supported by a stem section 679. Upon introduction of the top portion 677 into one of the two apertures 617a or 617b (for right-handed or left-handed use of the surgical tool, respectively), the segmented top portion 677 initially compresses inwardly to facilitate engagement within the respective aperture 617a (or 617b). Once the top portion 677 is fully engaged within aperture 617a (or 617b), the top portion 677 expands or "snaps" into engagement with a ring-like flange 619a (or 619b) disposed within the inner periphery of aperture 617a (or 617B). Preferably, the top portion 677 and the ring-like flange 619a (or 619b) are dimensioned to facilitate rotation of the surgical tool 600 relative to the hand clip 670 to allow a surgeon to select and orient the particular surgical tool 600 as needed during surgery (See FIG. 3C).

Figure 3F:
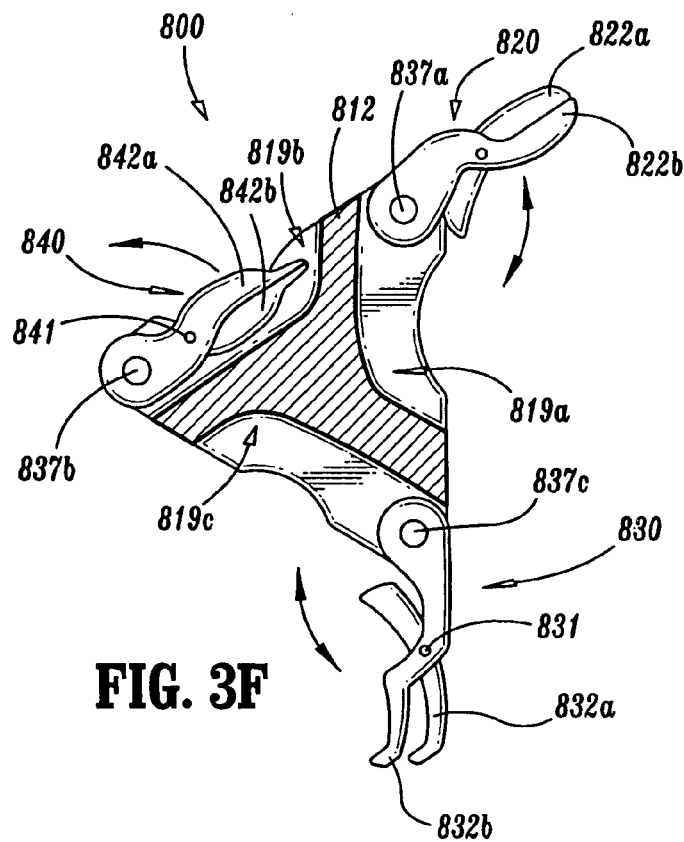
FIG. 3F shows another embodiment of the surgical tool according to the present invention wherein each of the plurality of surgical instruments is housed in a corresponding recess disposed along the outer periphery of the housing.
Figure 3E:
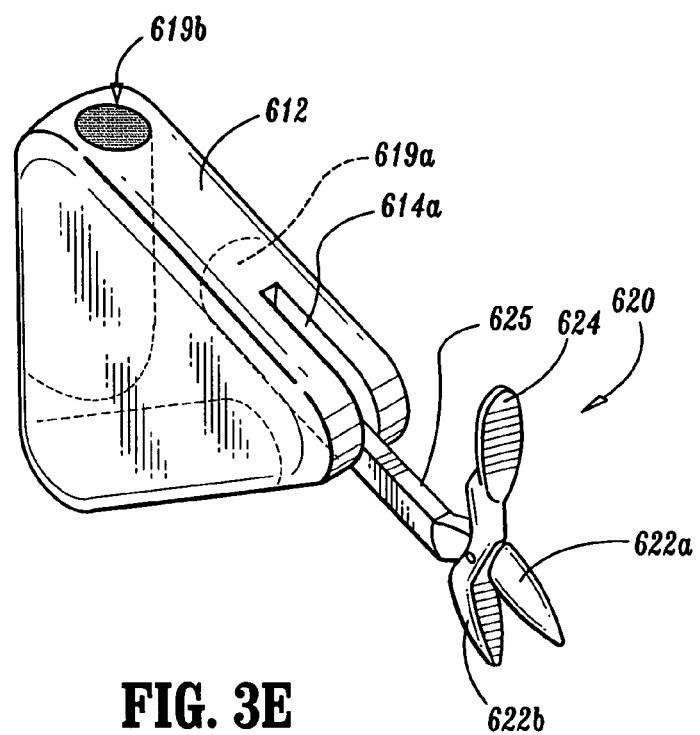
FIG. 3E is shows the embodiment of FIG. 3B with a surgical grasping instrument shown in a deployed configuration.

FIG. 3E shows the surgical tool 600 of FIG. 3B with a surgical grasping instrument 620 shown deployed from port 619a of housing 612 and ready for use. Much in the same (or similar) manner as described above with respect to the embodiment of FIGS. 1A–1D, the grasping instrument 620 includes a slide-like actuator 624 which moves along slot 614a to extend the shaft 625 and jaws 622a and 622b from the housing 612 to enable use of the grasping instrument 620 as needed during a surgical procedure.

FIG. 3F shows another embodiment of the surgical tool 800 according to the present disclosure wherein a plurality of surgical instruments 820, 830 and 840 are each housed in a corresponding recess 819a, 819b and 819c, respectively, disposed along the outer periphery of the housing 812. More particularly, each instrument, e.g., grasper 820, is rotatingly mounted to housing 812 about a pivot 837a and is selectively movable from a first "stored" position to a second "deployed" position. Preferably, each recess, e.g., 819a, is dimensioned to store the respective instrument, e.g., grasper 820, in a generally flush manner with respect to the outer periphery of the housing 812. Moreover, each recess 819A is preferably dimensioned such that the jaw members or end effectors 822a and 822b remain properly seated in a generally closed configuration when stored.

As can be appreciated, the other instruments of surgical tool 800 are deployed in much the same fashion as grasper 820 and include similar elements to those instruments described above. For example, instrument 830 is a curved forceps and includes jaws 832a and 832b which are rotatable about pivot 831 to approximate and grasp tissue. The forceps 830 mounts to housing 812 about pivot 837c and is stored within recess 819c when not is use. Likewise, scissors 840 include jaws 842a and 842b which are rotatable about pivot 841 to sever tissue. The scissors 840 mount to housing 812 about pivot 837b and are stored within recess 819b when not is use.

Figure 4A:
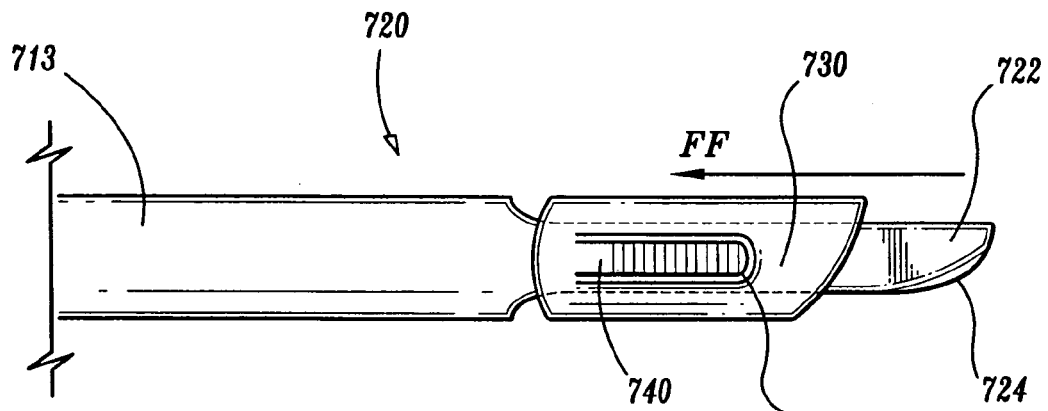
FIG. 4A is a side view of another embodiment of the present disclosure which shows a spring-biased blade guard for protecting a cutting blade of a scalpel.
Figure 4B:
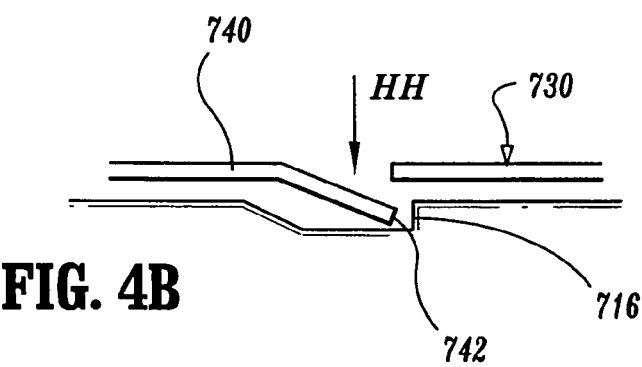
FIG. 4B is a schematic illustration of a locking mechanism for the blade guard of FIG. 4A which locks the blade guard in a retracted position to enable use of the cutting blade.
Figure 4C:
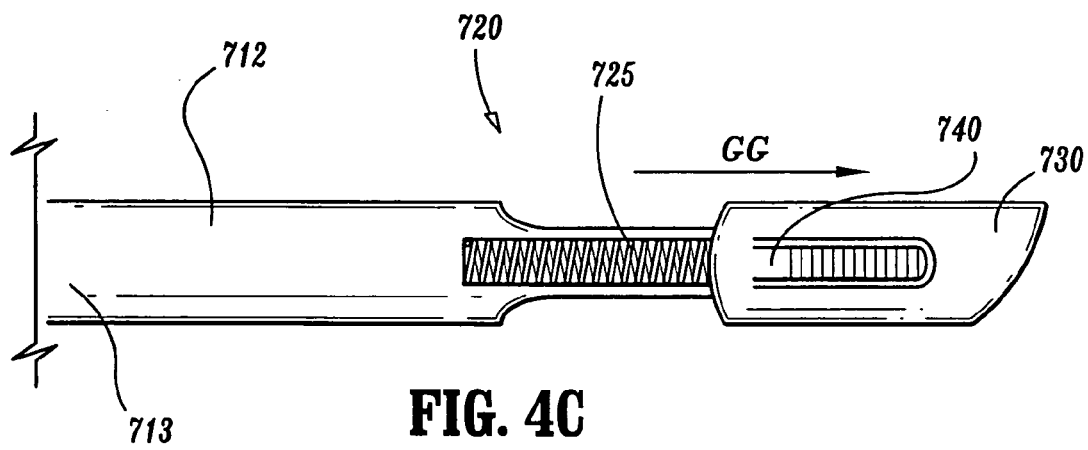
FIG. 4C is a side view of the embodiment of FIG. 4A showing the distal movement of the spring-biased blade guard after release of the locking mechanism.

As shown best in FIGS. 4A–4C, one of the plurality of instruments may be a surgical scalpel 720 having proximal and distal ends 713 and 722, respectively. The proximal end 713 is preferably dimensioned to slideably engage one of the ports (not shown) of the housing (not shown) and the distal end 722 includes a cutting edge 724. A spring-loaded safety guard 730 is also included which is movable relative to the scalpel 720 from a first position wherein the guard 730 substantially covers the cutting edge 724 of the scalpel 720 (See FIG. 4C) to a second position wherein the cutting edge 724 is exposed.

Preferably, the safety guard 730 includes a locking tab 740 for releasably locking the guard 730 in the second position (See FIG. 4B). The guard 730 may also include a spring 725 which automatically extends the guard 730 once the locking tab 740 is released to cover the cutting edge 724 when not in use. More particularly, during use the user retracts the guard 730 proximally against spring 725 in the direction "FF" and simultaneously depresses locking flange 740 inwardly (i.e., in the direction of arrow "HH") such that a distal end 742 of the locking tab 740 abuts against a corresponding flange or notch 716 disposed within the outer periphery of scalpel 730 (See FIG. 4B). The biasing force of the spring 725 retains the locking tab 740 within the notch 716 and locks the guard 730 in a retracted position to expose the cutting edge 724 of the scalpel 720 for use. Once the surgeon has completed the cut using the scalpel 720, the surgeon simply retracts the guard 730 proximally (i.e., in the direction "FF") which releases the locking tab 742 from the notch 716 and allows the guard 730 to extend distally in the direction "GG" over the cutting edge 724 under the force of the spring 725.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed:

1. A multi-instrument surgical tool, comprising:
   a) a housing having a plurality of ports disposed therein, said housing including a corresponding plurality of elongated channels each in communication with a respective one of said plurality of ports; and
   b) a plurality of surgical instruments mounted in said housing, at least one of said surgical instruments being slidably mounted in one of said plurality of ports for selective deployment from said housing;
   c) at least one of said instruments having a slide member attached to said instrument and accessible from an exterior of said housing; and
   d) one of said instruments includes a surgical scalpel which includes:
      proximal and distal ends, said proximal end being dimensioned to slideably engage one of said ports of said housing and said distal end having a cutting edge;
      a guard which is movable relative to said scalpel from a first position wherein said guard substantially covers the cutting edge of said scalpel to a second position wherein said cutting edge is exposed.

2. The tool of claim 1 wherein said guard includes a locking tab for releasably locking said guard in said second position.

3. The tool of claim 1 wherein said guard is spring-biased to return to said first position.

4. The tool of claim 1, wherein the housing includes a slot in communication with the elongated channel for receiving the slide member therethrough.

5. The tool of claim 4, wherein said elongated channel is open on an end of said housing and said slide member and said instrument is slidable in a distal direction in said channel by manipulation of said slide member so as to deploy said instrument from said channel.

6. The tool of claim 1, wherein said instruments are selected from the group consisting of: vessel sealing devices, dissectors, resectors, probes, morselators, ultrasonic instruments, video-assisted devices, clip appliers, surgical staplers, coagulators, irrigation instruments, and suction instruments.

7. The tool of claim 1, wherein the elongated channels are configured for interchanging different surgical instruments therein.

8. The tool of claim 7, wherein the elongated channels include a first set of channels dimensioned to accommodate a first category of surgical instruments and a second set of channels dimensioned to accommodate a second category of surgical instruments.

9. A multi-instrument surgical tool, comprising:
   a housing having a plurality of ports disposed therein, said housing including a corresponding plurality of elongated channels each in communication with a respective one of said plurality of ports;
   a plurality of surgical instruments mounted in said housing, each surgical instrument mounted in one of said plurality of ports for selective deployment from said housing; and
   a first instrument of said plurality of instruments comprising a locking flange and said housing having a locking post disposed in at least one of said channels, said locking flange being arranged to engage the locking post when said first instrument is stored within said housing.

10. The tool of claim 9, wherein said locking flange and said locking post are arranged so that upon movement of said first instrument proximally, said locking flange is released from said locking post.

11. A multi-instrument surgical tool, comprising:
   a) a housing having a plurality of ports disposed therein, said housing including at least one elongated channel in communication with said plurality of ports;
   b) said plurality of ports including a first port open at a first end of said housing and a second port open on a second end of said housing, said first end being opposite from said second end;
   c) a plurality of surgical instruments mounted in said housing, each surgical instrument being slidably mounted in said at least one elongated channel for selective deployment from said housing; and d) at least one of said instruments including a slide member attached to said instrument and accessible from an exterior of said housing, said housing including a slot in communication with the at least one elongated channel for receiving the slide member therethrough, said slot and said elongated channel are open on said first end of said housing and said slide member and said instrument are slidable in a distal direction in said channel by manipulation of said slide member so as to deploy said instrument from said channel.

12. The tool of claim 11, wherein said instruments are selected from the group consisting of: vessel sealing devices, dissectors, resectors, probes, morselators, ultrasonic instruments, video-assisted devices, clip appliers, surgical staplers, coagulators, irrigation instruments, and suction instruments.

13. The tool of claim 11, wherein the elongated channels are configured for interchanging different surgical instruments therein.

14. A multi-instrument surgical tool, comprising:
a) a housing having a plurality of ports disposed therein, said housing including at least one elongated channel in communication with said plurality of ports;
b) said plurality of ports including a first port open at a first end of said housing and a second port open on said first end of said housing; and
c) a plurality of surgical instruments mounted in said housing, each surgical instrument being slidably mounted in said at least one elongated channel for selective deployment from said housing;

d) at least one of said instruments including a slide member attached to said instrument and accessible from an exterior of said housing, said housing including a slot in communication with the at least one elongated channel for receiving the slide member therethrough, said slot and said elongated channel are open on said first end of said housing and said slide member and said instrument are slidable in a distal direction in said channel by manipulation of said slide member so as to deploy said instrument from said channel.

15. A multi-instrument surgical tool, comprising:
a) a plurality of housings movably mounted with respect to one another, each of said housings including a port in communication with an elongated channel; and
b) a plurality of surgical instruments, each surgical instrument being slidably mounted in one of said housings for selective deployment from said housing;
c) at least one of said instruments including a slide member attached to said instrument and accessible from an exterior of said housing, said housing including a slot in communication with the at least one elongated channel for receiving the slide member therethrough, said slot and said elongated channel are open on said first end of said housing and said slide member and said instrument are slidable in a distal direction in said channel by manipulation of said slide member so as to deploy said instrument from said channel.

* * * * *